United States Patent [19]

Suslow

[11] Patent Number: 4,584,274
[45] Date of Patent: Apr. 22, 1986

[54] BACTERIOPHAGE-RESISTANT PLANT GROWTH PROMOTING RHIZOBACTERIA

[75] Inventor: Trevor V. Suslow, Kensington, Calif.

[73] Assignee: The Regents of the University of California, Berkeley, Calif.

[21] Appl. No.: 465,082

[22] Filed: Feb. 9, 1983

[51] Int. Cl.$^4$ .................. C12N 1/20; C12N 15/00; C12R 1/40; A61K 37/00
[52] U.S. Cl. ......................... 435/253; 435/172.1; 435/877; 424/93; 47/58
[58] Field of Search ............... 435/240, 241, 253, 262, 435/267, 272, 874, 172.1, 948; 47/58; 424/93

[56] References Cited

U.S. PATENT DOCUMENTS 3,923,603 12/1975 Chakrabarty et al. ............... 195/78
4,218,534 8/1980 La Belle et al. ..................... 435/5

FOREIGN PATENT DOCUMENTS 0686707 9/1979 U.S.S.R. ............................ 435/253
0699016 11/1979 U.S.S.R. ........................... 435/253

OTHER PUBLICATIONS

Kloepper et al., *Current Microbiology*, v. 4, 1980, pp. 317–320, "Pseudomonas Sicterophores: A Mechanism Explaining Disease Suppressive Soils".

Teintze et al, *Biochemistry*, 1981, v. 20, pp. 6446–6457, "Structure of Ferric Pseudobactin, a Sicterophore from a Plant Growth Promoting Rhizobacteria".

Krylov et al, *Chem. Abst.*, vol. 94 (117689p) 1981, "Isolation and Characterization of Pseudomonas Putida Phagetesistant Mutantr by New Bacteriophages".

*Primary Examiner*—Thomas G. Wiseman
*Assistant Examiner*—Robin Lyn Teskin
*Attorney, Agent, or Firm*—Bertram I. Rowland

[57] ABSTRACT

Bacteriophage-resistant plant growth promoting rhizobacteria are employed for enhancing the yield of root crops, such as potatoes, sugar beets, radishes and the like, grown in soils which are infected by bacteriophage which limit the root colonization by the corresponding wild-type rhizobacteria.

The strain SH5 PR3 was deposited at the ATCC for patent purposes on Jan. 20, 1983, and granted Accession No. 39270.

1 Claim, No Drawings

BACTERIOPHAGE-RESISTANT PLANT GROWTH PROMOTING RHIZOBACTERIA

BACKGROUND OF THE INVENTION

Agricultural growers and researchers are constantly seeking means to economically improve root crop yields. One increasingly popular method involves the use of "beneficial" microorganisms which stimulate plant growth and improve crop yield.

A variety of mechanisms have been identified as being responsible for such plant growth promoting activity. For example, certain microorganisms directly enhance plant growth by producing growth hormones, which stimulate root crop growth directly, or by assisting in the uptake of nutrients by the crops. Alternatively, the beneficial microorganisms may promote growth indirectly by inhibiting the soil population of harmful microorganisms which limit root crop growth. Exemplary of such antagonistic microorganisms are those which produce antibiotics that kill the harmful micro-organisms and those which scavenge scarce soil nutrients in preference to the harmful microorganisms. The practice of inoculating the seeds or the soil with such beneficial microorganisms is generally referred to as "bacterization" regardless of the particular mechanism involved.

The efficacy of such beneficial microorganisms, referred to hereinafter as plant growth promoting rhizobacteria (PGPR), in promoting plant growth is highly dependent on their ability to successfully colonize the plant roots and the soil surrounding the roots (termed the "rhizosphere"). The ability of particular PGPR to colonize soil and promote plant growth is generally variable and dependent on the nature of the soil and on a number of environmental and biotic factors. It would be desirable to provide PGPR having improved capability to proliferate in different soil types which would, in turn, enhance the ability of the PGPR to promote root crop growth.

SUMMARY OF THE INVENTION

Novel methods and compositions for promoting the growth of root crops are provided. In particular, bacteriophage-resistant strains of plant growth promoting rhizobacteria (PGPR), are provided for enhanced rhizosphere colonization and plant growth promotant activity when compared to corresponding PGPR strains which lack phage resistance. Also, methods for their production and use are taught.

DESCRIPTION OF THE SPECIFIC EMBODIMENTS

Root crop production is enhanced and root crop diseases, such as root rot, are inhibited by treating the seeds, seed pieces, roots, and/or planting soil with bacteriophage-resistant strains of plant growth promoting rhizobacteria (PGPR). Such PGPR are particularly effective in promoting the growth of root crops which are planted in soils which can develop deleterious concentrations of soil-borne lytic bacteriophage that inhibit PGPR growth and limit rhizosphere colonization. The phage-resistant PGPR of the present invention are obtained by first isolating the interfering phage utilizing conventional screening techniques. Phage resistance is then introduced into one or more susceptible strains of PGPR by stressing the PGPR strain(s) with elevated levels of the isolated phage (i.e., phage concentrations higher than found in natural soils). By then isolating a DNA fragment which confers phage resistance from the resulting mutant strains, phage resistance can be further transmitted by genetic manipulation to susceptible PGPR or other microorganisms which are desired to display phage resistance.

The present invention is broadly applicable to any PGPR which are capable of enhancing the growth of root crops but susceptible to infection by bacteriophage which inhibit colonization of the rhizosphere. Such rhizobacteria (PGPR) may manifest any of the growth promotant mechanisms described above, including the production of growth hormones, the enhancement of the nutrient uptake by the root crops, the production of antibiotics which kill harmful soil microorganisms, and preferentially scavenging limited soil nutrients.

Such PGPR are typified by certain fluorescent pseudomonads, particularly those selected from *Pseudomonas fluorescens*, and *Pseudomonas putida*. Exemplary strains include BK1, TL3, SH5, A-1 (ATCC Accession No. 39168), B-10 (ATCC Accession No. 39169), and E6 (ATCC Accession No. 39167). The first three of these strains (BK1, TL3, and SH5) are on deposit with the U.S. Department of Agriculture, Agricultural Research Service, in Peoria, Ill., without restriction and are available to the public. The remaining strains are on deposit with the American Type Culture Collection, Rockville, Md., having the designated accession numbers. Other exemplary strains of PGPR include B4, B100, RV3, P182, P282, P382, and P482 available from the Culture Collection, University of California, Berkeley, Calif.

The bacteriophage-resistant PGPR strains of the present invention are obtained by first identifying soils suspected of harboring bacteriophage which interfere with the root colonization of a susceptible PGPR. The bacteriophage can be isolated from the soil by conventional techniques and employed at elevated concentrations to stress the particular PGPR or other susceptible bacteria. Mutant phage-resistant strains of the PGPR may then be selected.

Conveniently, the stress selection is carried out in growth media, as described in detail below. Alternatively, mutations can be induced in sterilized soil by inoculating the soil with a higher than natural concentration of the isolated phage, typically above $10^2$pfu(plaque forming units)/gm soil, more typically above $10^3$pfu/gm soil, usually above $10^5$pfu/gm soil. In either case, spontaneous mutants may be selected which are phage-resistant and which can be used to promote the growth of root crops which are planted in soils harboring the isolated phage (or other similar phage to which resistance has been imparted).

Certain soils may harbor two or more types of deleterious bacteriophage which interfere with the colonization of a particular PGPR. Resistance to each type of phage may be separately imparted to the susceptible PGPR. After isolating each of the phage, mutant PGPR resistant to a first type of phage may be obtained by the conventional stressing techniques just described. The resistant strain may then be further stressed to acquire resistance to the second and subsequent phage types until the PGPR has acquired an appropriate spectrum of phage resistance to colonize the soil of interest.

To isolate a deleterious bacteriophage from soil suspected of containing such phage, root crop seeds are treated with a susceptible PGPR (or other susceptible rhizobacteria) and planted in the infected soil maintained near field moisture capacity. After allowing the seeds to germinate and grow, typically for a period of several weeks, roots are removed from the seedlings, and the PGPR or other rhizobacteria isolated by dilution-series plating on a suitable growth medium. If bacteriophage is present in the soil, phage plaques will be observed in the developing bacterial colonies. The bacteriophage may be isolated by removing specimens of the infected bacteria from the developing colonies and transferring them into an appropriate buffer. The resulting suspensions are agitated to release the phage from the infected bacteria, and the bacteria cells separated by centrifugation. The supernatants, containing the phage, may then be filtered to remove the remaining contaminants, leaving a high titer stock of the phage.

Using the high titer phage stock, mutant PGPR strains can be induced by conventional techniques. Conveniently, the PGPR and the isolated phage are mixed at a weight ratio of from about 100:1 to about 10,000:1, usually about 1,000:1, and grown in an appropriate media. The culture is then plated, and resistant mutants are selected from viable colonies which develop centrally to the clear areas of phage plaques. Resistant mutants are then purified by single colony selection.

Such phage-resistant PGPR are suitable for incorporation in the plant growth promoting compositions described below. Additionally, these phage-resistant strains can provide a source for obtaining the DNA fragment(s) which confer phage resistance. Such DNA fragment(s) are obtained either by random fragmentation of the genome or by synthesis of cDNA from mRNA. The isolated DNA fragment(s) can then be introduced to susceptible PGPR by conventional techniques.

Alternatively, DNA fragment(s) which confer phage resistance may be obtained from the phage itself. For example, repressor genes which regulate the production of protein(s) essential to phage growth can be isolated and introduced in the PGPR on a suitable vector. By constructing the vector to provide high levels of repressor, production of the essential protein(s) can be inhibited and multiplication of the phage blocked.

The DNA fragment(s) conferring phage resistance can be isolated from the chromosomal DNA of a phage-resistant mutant rhizobacteria strain by well-known techniques. Typically, high molecular weight DNA is obtained by first lysing the bacterial cells in a detergent, such as sodium dodecyl sulfate, which denatures and inactivates the DNAses. The proteins are then extracted in an organic solvent, typically phenol, and the RNA separated by buoyant density centrifugation. Alternatively, the nucleic acids can be concentrated by ethanol precipitation and the RNA removed by digestion with RNAses. Purified DNA may then be obtained by reprecipitation.

After obtaining the high molecular weight DNA, a gene library can be developed using conventional methods. Conveniently, the high molecular weight DNA is partially digested to produce fragments having a preselected average length, selected depending on the contemplated cloning vector. It is usually desirable to enrich those fragments in the desired size range by well-known chromatographic methods.

The resulting DNA fragments are then inserted into suitable cloning vectors which are introduced into a compatible host. Since the DNA fragments are of bacterial origin, it is convenient to use a common plasmid vector, such as pBR322 or pBR325, although various phage vectors and cosmids would also be suitable. Transformants may be selected based on a selective marker characteristic of the vector employed. The transformants are further screened for resistance to the isolated bacteriophage, and the positive colonies cloned to provide a source for the DNA fragment(s) which confers phage resistance. For such screening, it will be necessary to employ a host which is susceptible to the isolated phage. Conveniently, the PGPR itself may be employed, requiring the selection of an appropriate vector. In the case of pseudomonad hosts, derivatives of plasmid RSF1010, such as pKT212 and pKT214, are particularly useful. The DNA sequences may be inserted at unique BamHI and BglII sites, and selection based on loss of $Tc^r$.

By introduction of the isolated DNA fragment(s) just described, phage resistance can be conferred on susceptible PGPR. Alternatively, phage resistance may be enhanced in PGPR which are already phage-resistant, typically by introducing multiple copies of the DNA fragment(s).

The DNA fragment(s) can be introduced directly into the PGPR genome, or can be first incorporated into a vector which is then introduced into the PGPR. Exemplary methods of direct incorporation include transduction by recombinant phage or cosmids, transfection where specially treated PGPR can be caused to take up naked phage chromosomes, transformation by calcium precipitation, and conjugation. Exemplary vectors include plasmids, cosmids and phages. As stated above, broad host spectrum derivatives of RSF1010 are particularly useful for transforming pseudomonad PGPR.

In general, the bacteriophage-resistant PGPR strains of the present invention are applied, alone or in combination with one or more other PGPR strains, to seeds, seed pieces, or roots of root crops, such as potatoes, sugar beets, radishes and the like, in concentrations from about $10^5$ to about $10^9$ cells/ml of an agronomically-acceptable liquid carrier medium. A paste may be used to apply to the seeds at concentrations of $10^{10}$ cells/ml or greater. While it is preferred to apply the PGPR of the present invention directly to the seeds, seed pieces or roots prior to planting, the subject microorganisms can be used to colonize soil in the vicinity of planting prior to planting. In particular, they may be used to recolonize soil which has been fumigated or pasteurized.

The PGPR strains of this invention may be utilized effectively in diverse plant growth promoting compositions, including agronomically-acceptable adjuvants and carriers normally employed for facilitating the dispersion of active ingredients for agricultural applications, recognizing as known that the dosage, formulation, mode of application, and other variables may effect the activity of the PGPR in any given application. Thus, the previously described phage-resistant PGPR may be formulated as a suspension or dispersion, in aqueous or non-aqueous media, as a dust, as a wettable powder, as an emulsifiable concentrate, as a granule, or as any of several other known types of formulations, depending on the desired mode of application. These compositions may be applied as sprays, dusts, or granules to the seeds, seed pieces, roots, plants, soil, or plant situs against which activity is desired.

In order to provide compositions of the form of dust, granules, water dispersed powders, aqueous dispersions, or emulsions and dispersions in organic liquids, the carrier or diluent agent in such formulations may be a finely divided solid, an organic liquid, water, a wetting agent, a dispersing agent, or an emulsifying agent, or any suitable combination of these. Generally, when liquids and wettable powders are prepared, a conditioning agent comprising one or more surface-active agents or surfactants is present in amounts sufficient to render a given composition containing the PGPR dispersible in water or in oil.

The PGPR of the present invention are obtained as described above and cultured by standard fermentation procedures. To convert the desired PGPR to a form which will facilitate the preparation of the following described compositions, a slurry is prepared which is then dried onto a primary, agronomically-acceptable carrier, such as vermiculite, whereby the microorganism is adsorbed onto the carrier. The microorganism, adsorbed onto the carrier, becomes the concentrate for preparing the desired composition.

The surface-active agent used can be a wetting, dispersing, or emulsifying agent which will assist dispersion of the effective composition. The surface-active agent or surfactant can include such anionic, cationic, and nonionic agents as have heretofore been generally employed in plant control compositions of similar types. Suitable surface-active agents are described in, for example, "Detergents and Emulsifiers", 1971 Annual by John W. McCutcheon, Inc.

In general, 1-10 percent by weight of the surface-active agent will be used in compositions of this invention and ordinarily the amount of surface-active agent will range from 1-5 percent, but may be even less than 1 percent by weight.

Additional surface-active agents can be added to formulations to increase the ratio of surfactants: active ingredients up to as high as 5:1 by weight. Such compositions may have a greater biological effectiveness than can be expected when the components are used separately. When used at higher ratios, it is preferred that the surfactant be present in the range of about 1/5 to 5 parts surfactant for each part of active agent.

In the Experimental section, a particular bacteriophage designated PQ was isolated from soil obtained from a location near Shafter, Calif. The phage PQ was found to infect PGPR strains SH5$_{RN}$, B4 and B100, and was found not to infect certain other rhizobacteria. The phage PQ was used to obtain five phage-resistant mutants of strain SH5$_{RN}$, each of which (in contrast to wild-type SH5$_{RN}$) were found to provide plant growth promoting activity in soils infected with phage PQ. The isolation of phage PQ and recovery of the particular phage-resistant mutants are exemplary of the methods and compositions of the present invention. The invention, however, is not limited to the particular phage or PGPR, and instead applies broadly to all types of PGPR and the various bacteriophage which can infect these PGPR to limit their ability to colonize the rhizosphere of root crops and to provide growth promoting activity.

The following examples are offered by way of illustration and not by way of limitation.

EXPERIMENTAL

The Growth Medium employed in the following experiments is King's medium B supplemented with 100 μg/ml rifampicin and 100μ g/ml cycloheximide as described by Suslow and Schroth (1982) Phytopath. 72:199-206. Bacterial strain SH5$_{RN}$ is a fluorescent pseudomonad resistant to rifampicin and nalidixic acid and available from the Culture Collection, University of California, Berkeley, Calif. Hesperia Fine Sandy Loam (HSL) is soil obtained from a field near Shaftner, Calif. Phosphate Washing Buffer (PWB) is Bacto ® peptone (1 gm), KH$_2$PO$_4$ (6.25 gm), K$_2$H$_2$PO$_4$.3H$_2$O (11.8 gm) in one liter of water. The following additional abbreviations are used: cfu: colony-forming units; and pfu: plaque-forming units.

1. Bacteriophage Isolation

Sugar beet seeds (c.v. USH11) were pelleted with SH5$_{RN}$ in a diatomaceous earth-cellulose methyl ether carrier as described by Suslow and Schroth (1982) Phytopath., supra, to a population density of about 10$^8$cfu/seed and planted in clay pots containing 125 cm$^3$ of HSL suspected of containing bacteriophage. After allowing the seeds to grow for several weeks, roots were removed and the SH5$_{RN}$ isolated by dilution-series plating on Growth Medium. Numerous phage plaques were revealed in the developing colonies which substantially reduced the population densities of the SH5$_{RN}$.

Bacteriophage were isolated from the Growth Medium by aseptically removing agar plugs (see, Adams, *Bacteriophages*, Interscience, New York (1959) p. 592) and transferring them into PWB at about 5 ml per 2 cm$^2$ agar plug. The agar plugs were intermittently agitated in a vortex mixer for 5 minutes, and the supernatants transferred into individual microcentrifuge tubes. The tubes were centrifuged to separate the bacterial cells from the mixture, leaving the phage suspended. The phage suspensions were then passed through a 25 μm filter, and the filtrates added to PWB (10 ml). The resulting high titer stock was stored over 0.1% chloroform at 4° C. Prior to storage, the phage was determined to be chloroform insensitive.

After storage, virulence of the phage was tested by adding high titer stock (0.1 ml) to PWB (9.9 ml) and then transferring 0.1 ml of the mixture to PWB (9.9 ml) containing 10$^8$cfu SH5$_{RN}$/ml. Dilution end-point tests were made using single and double layer agar methods. Billings, "Isolation, Growth and Preservation of Bacteriophages", *Methods in Microbiology*, Norris and Ribbons, eds., Academic Press, New York (1969) p. 369. The phage was designated PQ.

2. Selection of Resistant Mutants

Strain SH5$_{RN}$ Pseudomonas putida and phage PQ were mixed in molten Growth Medium at about 1000:1 by weight and poured as an overlay on Growth Medium. Resistant mutants were selected from colonies which developed centrally to the clear area of phage plaques and purified by single colony selection. Resistance was verified by cross-streaking several of the isolated strains against PQ on Growth Medium and determining if lysis occurred. Vidaver (1976) Ann. Rev. Phytopath. 14:451-465. Five strains designated SH5 PR1 through SH5 PR5 were confirmed as being resistant to phage PQ. Strain SH5 PR3 was deposited at the A.T.C.C. on Jan. 20, 1983, and granted Accession No. 39270.

3. Greenhouse Colonization Trials

The ability of the phage-resistant strains to colonize roots and promote plant growth in the presence of phage PQ was compared to that of the wild-type SH5$_{RN}$. Sugar beet seeds (c.v. USH11) were pelleted with SH5$_{RN}$, SH5 PR1, SH5 PR2, SH5 PR3, SH5 PR4 and SH5 PR5 as described hereinabove. Pelleted seeds and untreated (control) seeds were planted in clay pots containing 125 cm$^3$ of either natural HSL or twice-autoclaved HSL.

Table 1 sets forth the results of a first experiment where both treated and untreated seeds were planted in natural (not autoclaved) soil inoculated with PQ. Three seeds were planted in each pot and the combined growth of the resulting three seedlings was measured after three weeks. The average growth values for ten replications of each treatment indicate that treatment with the wild-type SH5$_{RN}$ provides only marginal growth promotion (approximately 9%) while treatment with the phage-resistant mutant strains of SH5$_{RN}$ provides substantial growth promotion ranging from approximately 86% to over 130%.

TABLE 1

| Treatment[3] | Growth[1] in Natural HSL Treated with PQ[2] | | | | | | | | | | | Increase Over Control | Increase Over SH5$_{RN}$ |
|---|---|---|---|---|---|---|---|---|---|---|---|---|---|
| | Replication | | | | | | | | | | Average | | |
| | A | B | C | D | E | F | G | H | I | G | | | |
| None (control) | 2.7 | 2.2 | 3.1 | 2.3 | 1.2 | 2.7 | 1.3 | 2.4 | 2.4 | 1.9 | 2.2 | — | — |
| SH5$_{RN}$ | 1.9 | 2.9 | 2.2 | 3.5 | 1.4 | 1.6 | 2.5 | 3.1 | 2.4 | 3.0 | 2.4 | 9% | — |
| SH5 PR1 | 3.5 | 3.3 | 4.2 | 5.9 | 5.3 | 4.7 | 4.1 | 3.9 | 3.7 | 5.5 | 4.4 | 91% | 83% |
| SH5 PR2 | 4.1 | 4.7 | 5.4 | 5.7 | 4.2 | 5.6 | 4.7 | 3.8 | 5.2 | 5.0 | 4.8 | 118% | 100% |
| SH5 PR3 | 3.7 | 6.5 | 5.5 | 4.9 | 4.2 | 5.3 | 6.1 | 5.1 | 5.4 | 4.4 | 5.1 | 131% | 113% |
| SH5 PR4 | 5.8 | 3.9 | 3.7 | 2.7 | 4.7 | 3.9 | 3.9 | 5.1 | 4.2 | 3.5 | 4.1 | 86% | 71% |

[1]Growth measured as combined weight (gms) of three seedlings measured at three weeks after emergence.
[2]10$^6$ pfu/gm soil
[3]10$^8$ cfu/ml (10$^6$ cfu/seed)

Table 2 describes the results of a second, similar experiment with growth measured after six weeks in natural (not autoclaved) soil. Again, the seeds treated with the phage-resistant strains of SH5$_{RN}$ provided substantial growth promotion when compared to untreated seeds and those treated with wild-type SH5$_{RN}$.

TABLE 2

| Treatment[3] | Growth[1] in Natural HSL Treated with PQ[2] | | | | | | | Increase Over Control | Increase Over SH5$_{RN}$ |
|---|---|---|---|---|---|---|---|---|---|
| | Replication | | | | | | Average | | |
| | A | B | C | D | E | F | | | |
| None (control) | 4.7 | 6.2 | 4.0 | 3.5 | 6.3 | 5.9 | 5.1 | — | — |
| SH5$_{RN}$ | 3.5 | 4.9 | 7.0 | 7.1 | 4.3 | 5.2 | 5.3 | 4% | — |
| SH5 PR1 | 7.0 | 8.3 | 9.1 | 8.7 | 7.7 | 5.9 | 7.7 | 51% | 45% |
| SH5 PR2 | 8.7 | 8.1 | 9.0 | 5.8 | 6.6 | 6.7 | 7.4 | 45% | 40% |
| SH5 PR3 | 8.5 | 7.3 | 7.0 | 7.2 | 6.9 | 6.7 | 7.3 | 43% | 38% |
| SH5 PR4 | 6.5 | 7.5 | 6.9 | 7.2 | 8.9 | 9.5 | 7.8 | 53% | 47% |
| SH5 PR5 | 7.4 | 7.0 | 6.3 | 5.9 | 4.7 | 5.9 | 6.2 | 22% | 17% |

[1]Growth measured as combined weight of three seedlings measured at six weeks after emergence
[2]10$^5$ pfu/gm soil
[3]10$^8$ cfu/ml (10$^6$ cfu/seed)

Table 3 compares the proliferation of wild-type SH5$_{RN}$ and phage-resistant mutant SH5 PR3 in the presence of phage PQ. As a control, seeds treated with SH5$_{RN}$ were also planted in autoclaved soil without addition of PQ. Root colonization was determined weekly for five weeks (six replications). The results indicate that colonization by the wild-type SH5$_{RN}$ in the sterile soil was substantially the same as colonization of the phage-resistant strain in the soil inoculated with PQ. Colonization by the wild-type strain in the phage-infected soil, however, was substantially less in all cases.

TABLE 3

| Treatment[2] | PQ Added[3] | Week | Proliferation[1] of SH5$_{RN}$ and SH5 PR3 in Autoclaved HSL with and without PQ | | | | | |
|---|---|---|---|---|---|---|---|---|
| | | | Replication | | | | | |
| | | | A | B | C | D | E | F |
| SH5$_{RN}$ | No | 1 | 8 × 10$^5$ | 1 × 10$^5$ | 6 × 10$^3$ | 6 × 10$^5$ | 1 × 10$^4$ | 2 × 10$^4$ |
| | | 2 | 4 × 10$^5$ | 9 × 10$^4$ | 2 × 10$^3$ | 4 × 10$^5$ | 3 × 10$^4$ | 9 × 10$^3$ |
| | | 3 | 3 × 10$^5$ | 7 × 10$^4$ | 8 × 10$^3$ | 9 × 10$^4$ | 8 × 10$^3$ | 9 × 10$^3$ |
| | | 4 | 4 × 10$^5$ | 2 × 10$^5$ | 6 × 10$^3$ | 8 × 10$^4$ | 2 × 10$^3$ | 4 × 10$^4$ |
| | | 5 | 8 × 10$^5$ | 2 × 10$^5$ | 4 × 10$^3$ | 3 × 10$^5$ | 4 × 10$^4$ | 7 × 10$^3$ |
| SH5$_{RN}$ | Yes | 1 | 2 × 10$^2$ | 3 × 10$^2$ | 1 × 10$^3$ | 6 × 10$^2$ | 2 × 10$^2$ | 9 × 10$^1$ |
| | | 2 | 3 × 10$^2$ | 1 × 10$^2$ | 5 × 10$^2$ | 7 × 10$^2$ | 1 × 10$^2$ | 9 × 10$^1$ |
| | | 3 | 6 × 10$^2$ | 9 × 10$^1$ | 5 × 10$^2$ | 2 × 10$^3$ | 9 × 10$^1$ | 7 × 10$^1$ |
| | | 4 | 1 × 10$^3$ | 5 × 10$^2$ | 9 × 10$^1$ | 1 × 10$^3$ | 5 × 10$^2$ | 2 × 10$^2$ |
| | | 5 | 2 × 10$^2$ | 3 × 10$^3$ | 1 × 10$^2$ | 6 × 10$^2$ | 8 × 10$^2$ | 3 × 10$^2$ |
| SH5 PR3 | Yes | 1 | 9 × 10$^5$ | 9 × 10$^4$ | 7 × 10$^4$ | 1 × 10$^5$ | 2 × 10$^4$ | 1 × 10$^4$ |
| | | 2 | 7 × 10$^5$ | 8 × 10$^5$ | 9 × 10$^4$ | 2 × 10$^5$ | 3 × 10$^4$ | 9 × 10$^3$ |
| | | 3 | 1 × 10$^6$ | 2 × 10$^5$ | 2 × 10$^4$ | 8 × 10$^4$ | 9 × 10$^3$ | 7 × 10$^3$ |
| | | 4 | 8 × 10$^5$ | 6 × 10$^5$ | 2 × 10$^4$ | 9 × 10$^4$ | 9 × 10$^3$ | 9 × 10$^3$ |
| | | 5 | 4 × 10$^5$ | 3 × 10$^5$ | 6 × 10$^4$ | 1 × 10$^5$ | 5 × 10$^4$ | 3 × 10$^3$ |

[1]Measured as cfu/cm root
[2]5 × 10$^8$ cfu/ml (5 × 10$^7$ cfu/seed)
[3]5 × 10$^7$ pfu/gm soil 4. Phage Host Range Beneficial rhizobacteria and phytopathogenic bacteria were treated for sensitivity to phage PQ. Double-layer agar and phage-typing methods were used. The results are presented in Table 4 where (+) indicates sensitivity, (−) indicates no sensitivity, and (±) indicates marginal sensitivity.

TABLE 4

Sensitivity of Various Bacteria to Phage PQ

| Rhizobacteria | | Phytopathogens | |
|---|---|---|---|
| SH5 | + | P. syringae | − |
| B4 | + | P. savastanoi | − |
| B100 | + | P. phaseolicola | − |
| RV3 | − | P. marginalis | ± |
| B1O | − | P. tomato | ± |
| E6 | − | E. carotovora | − |
| P182 | − | E. atroseptica | − |
| P282 | − | E. chrysanthemi | − |
| P382 | − | Wasco 9 | ± |
| P482 | − | SB24 | ± |

[1]Obtained from the Culture Collection at the University of California, Berkeley, California.

The above experiments demonstrate that phage-resistant strains of PGPR may be obtained by stress mutation under conditions of elevated phage concentrations. Such phage-resistant PGPR strains are better able to colonize the rhizosphere of plants growing in phage-infected soil and, as a result, provide substantially enhanced growth promoting activity compared to their wild-type counterparts.

Although the foregoing invention has been described in some detail by way of illustration and example for purposes of clarity and understanding, it will be obvious that certain changes and modifications may be practiced within the scope of the appended claims.

What is claimed is:

1. A biologically pure culture of *Pseudomonas putida* SH5 PR3, American Type Culture Collection Accession No. 39270.

* * * * *